US012805916B2

(12) United States Patent
O'Donnell et al.

(10) Patent No.: US 12,805,916 B2
(45) Date of Patent: Nov. 24, 2026

(54) INTERPHALANGEAL JOINT IMPLANT METHODS AND APPARATUS

(71) Applicant: TOETAL SOLUTIONS INC., Malvern, PA (US)

(72) Inventors: Jeffrey O'Donnell, Malvern, PA (US); William Rhoda, Media, PA (US); Richard Briganti, Bala Cynwyd, PA (US); Nicholas Romansky, Malvern, PA (US); Stephen Soondar, Devon, PA (US); Peter Datcuk, Jr., Quakertown, PA (US)

(73) Assignee: Toetal Solutions Inc., Malvern, PA (US)

( * ) Notice: Subject to any disclaimer, the term of this patent is extended or adjusted under 35 U.S.C. 154(b) by 0 days.

(21) Appl. No.: 18/844,099

(22) PCT Filed: Mar. 15, 2023

(86) PCT No.: PCT/US2023/015296

§ 371 (c)(1),
(2) Date: Sep. 5, 2024

(87) PCT Pub. No.: WO2023/177741

PCT Pub. Date: Sep. 21, 2023

(65) Prior Publication Data

US 2025/0177017 A1 Jun. 5, 2025

Related U.S. Application Data

(60) Provisional application No. 63/321,404, filed on Mar. 18, 2022.

(51) Int. Cl.
*A61B 17/02* (2006.01)
*A61B 17/72* (2006.01)

(52) U.S. Cl.
CPC ...... *A61B 17/7266* (2013.01); *A61B 17/7291* (2013.01)

(58) Field of Classification Search
CPC .............. A61B 17/921; A61B 17/7258; A61B 17/7275; A61B 17/7291; A61B 17/7266
See application file for complete search history.

(56) References Cited

U.S. PATENT DOCUMENTS 3,986,504 A * 10/1976 Avila ................. A61B 17/7266 606/63
6,575,973 B1 * 6/2003 Shekalim ........... A61B 17/7266 606/68

(Continued)

FOREIGN PATENT DOCUMENTS

AU 2014 209124 A1 9/2015
FR 2633345 A1 * 12/1989 ......... A61B 17/7266
GB 2421187 A * 6/2006 ......... A61B 17/7266

OTHER PUBLICATIONS

PCT International Search Report for PCT/US2023/15296 dated Jun. 2, 2023, in 2 pages.

(Continued)

*Primary Examiner* — Jan Christopher L Merene
(74) *Attorney, Agent, or Firm* — Knobbe, Martens, Olson & Bear, LLP

(57) ABSTRACT

A method and apparatus for correcting abnormal flexion of the joints of the human foot, hand or stabilization of other human tissues.

32 Claims, 5 Drawing Sheets

(56) References Cited

U.S. PATENT DOCUMENTS

| | | | | |
|---|---|---|---|---|
| 2001/0000186 | A1 | 4/2001 | Bramlet et al. | |
| 2002/0068936 | A1 | 6/2002 | Burkus et al. | |
| 2004/0106996 | A1 | 6/2004 | Liu et al. | |
| 2005/0049590 | A1 | 3/2005 | Alleyne et al. | |
| 2006/0229617 | A1 | 10/2006 | Meller et al. | |
| 2008/0177262 | A1 | 7/2008 | Augoyard et al. | |
| 2010/0131014 | A1 | 5/2010 | Peyrot et al. | |
| 2013/0211451 | A1 | 8/2013 | Wales et al. | |
| 2014/0188179 | A1 | 7/2014 | McCormick | |
| 2014/0214080 | A1* | 7/2014 | Wales ................ | A61B 17/8869 606/232 |
| 2015/0230843 | A1 | 8/2015 | Palmer et al. | |
| 2016/0015437 | A1* | 1/2016 | Elleby ................ | A61B 17/7291 606/329 |
| 2016/0317198 | A1 | 11/2016 | Fox | |
| 2017/0100171 | A1 | 4/2017 | Palmer et al. | |
| 2017/0290655 | A1 | 10/2017 | Piccirillo et al. | |
| 2022/0031301 | A1 | 2/2022 | Rippe et al. | |

OTHER PUBLICATIONS

PCT International Written Opinion for PCT/US2023/15296 dated Jun. 2, 2023, in 5 pages.
Extended European Search Report dated May 12, 2026, in 15 pages.

* cited by examiner

INTERPHALANGEAL JOINT IMPLANT METHODS AND APPARATUS

BACKGROUND OF THE INVENTION

This disclosure relates to a method and apparatus for correcting abnormal flexion of the joints of the human foot (or of the hand, or in other embodiments, other areas needing stabilization or fixation.) More particularly, this disclosure relates to a combination of dorsiflexion of the metatarsal/proximal phalangeal joint and plantar flexion of the proximal interphalangeal joint, commonly called a hammer toe.

The lesser toes of the human foot are composed of three bones and contain two joints. The three toe bones are a proximal phalanx (closest to the metatarsal bone), a middle phalanx, and a distal phalanx (at the end of the toe). The three toe bones are connected by two toe joints, a proximal interphalangeal joint (PIP), which is formed by a distal end of the proximal phalanx and a proximal portion of the middle phalanx; and a distal interphalangeal joint (DIP), distal to the PIP and formed by a distal end of the middle phalanx and a proximal end of the distal phalanx.

Contraction of the lesser toes of the foot is a common pathologic condition due to an imbalance between the tendons on the top and bottom of the toe(s). When an affected toe is able to be straightened out manually, i.e. by an individual or an eternal force, it is referred to as a flexible hammer toe. If left untreated these flexible contractures will become a fixed deformity know as a rigid hammer toe, which typically cannot be put back into normal alignment. The PIP is more implicated in a hammer toe syndrome deformity then the DIP.

There are many palliative modalities such as pads and various forms of orthodigital devices used to accommodate toe deformities. Those conservative options, however, often do not provide an afflicted individual with sufficient comfort and in some cases are unpreferred, given the fact that various alternative surgical options are available.

Throughout the history of performing toe surgery many methods have been attempted by surgeons ranging from simple tendon release, partial joint excision, full joint excision and, as a final resort, complete fusion (arthrodesis) of a joint rendering a straight toe. Arthrodesis of the joint is usually reserved for severe deformities or in cases where previous non-arthrodesis procedures were performed but failed to provide a patient with a desired outcome.

In the prior art, some surgeons fused the PIP joint by a simple end-to-end method. In this procedure a surgeon resects the articular cartilage of the end of one toe bone and the base of an adjoining bone which forms an abnormal joint. The two ends are approximated to each other with the expectation that they will fuse together. An inherent problem with this method is a high rate of non-union with possible recurrence of deformity.

Another prior art method is to insert a smooth pin or wire that extends out of the distal end of the toe. The wire is used to hold the ends of the bones in alignment until fusion occurs. Because these wires and pins are smooth, however, it is possible for the joint to distract, leading to a failure or non-union.

Additionally, yet another prior art method was developed which utilized a thin screw inserted from the tip of a toe across the joint. The purpose of this device was to provide compression which facilitates end-to-end fusion. The insertion of a specialized screw is difficult to perform and presents a possibility of damaging the DIP. Furthermore, when the pin is removed it requires a second surgical procedure.

Yet another prior art device was developed utilizing "memory" metal that was simply inserted into either the DIP or PIP after resection of the joint. These devices are relatively expensive when compared to pins, wires, or screws and also have been known to sometimes expand too quickly rending the device ineffective.

Finally, a prior art hinged toe fusion device was developed to replace the PIP. Each end of the device was inserted into a corresponding end of the bones flanking the PIP. A limitation with this device is that it is relatively difficult to work with. The two components are not designed to be easily separated. Also, the device can be difficult to properly align and can rotate out of the proper position after insertion. Also, it does not allow for the additional use of a pin or wire to be inserted across the metatarsophalangeal joint (MP), the joint proximal to the PIP, which is sometimes desirable.

Regardless of which prior art fixation method is employed, it is sometimes necessary to revise the surgical intervention, or to entirely remove it, and most prior art devices are difficult to revise or remove, particularly after they have been in place for some time.

The difficulties and limitations suggested in the preceding prior art descriptions are not intended to be exhaustive, but rather are among many which demonstrate that although significant attention has been devoted to surgically correcting hammer toe disfigurement, nevertheless surgical implants and procedures appearing in the past will admit to worthwhile improvement.

BRIEF SUMMARY OF PREFERRED EMBODIMENT

The subject disclosure includes advantages of bone fusion while simplifying the procedure and decreasing or eliminating incidences of non-union and non-alignment prevalent in the prior art. A cylindrical element is placed to bridge a surgically prepared joint and is locked in place by extending tines that engage the inner surface of the phalanges in a manner than prevents subsequent disengagement or rotation. Optionally, elements permitting retraction of the tines may be provided to facilitate revision or removal of the cylindrical element. Also optionally, the cylindrical element is provided with ridges or stops on its external surface that prevent over-insertion of the element into the bone, as well as unintended rotation after placement.

THE DRAWINGS

Numerous advantages of the present disclosure will become apparent from the following detailed description of preferred embodiments taken in conjunction with the accompanying drawing wherein.

DETAILED DESCRIPTION OF THE INVENTION

Figure 1B:
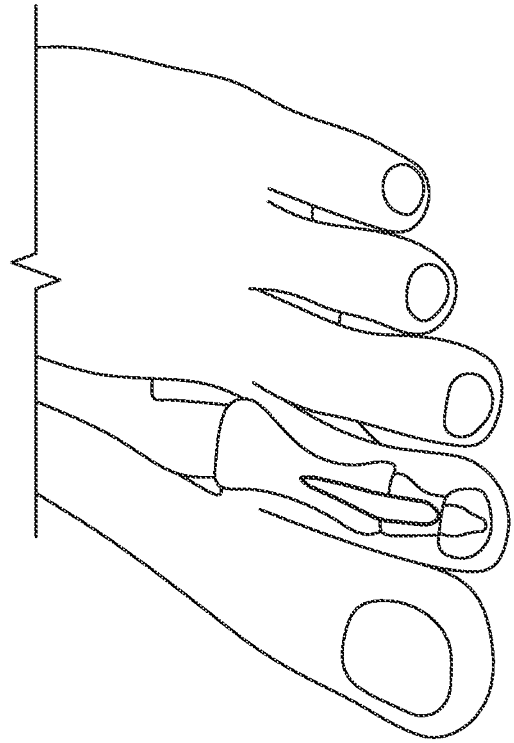
FIG. 1 is a schematic representation of a human foot showing the second toe as having "hammertoe" in FIG. 1*a*, and after implantation of the device of the present invention, as having the condition resolved in FIG. 1*b*.
Figure 1A:
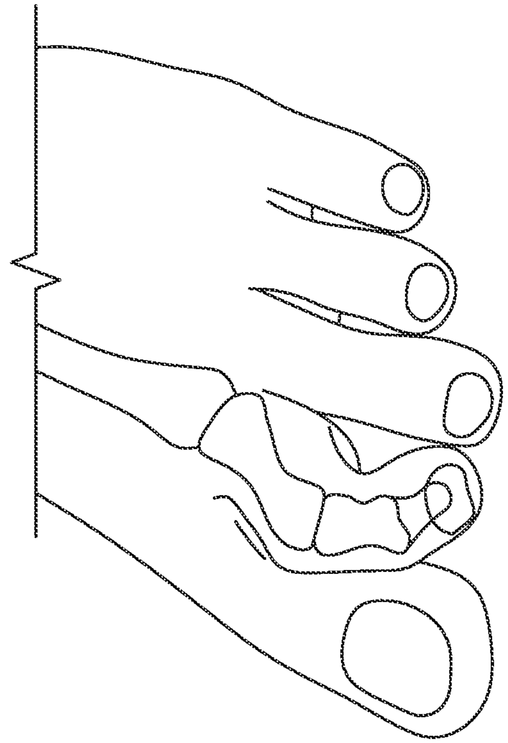

Referring now particularly to the drawings, wherein like reference characters refer to like parts, and to FIG. 1, there will be seen a depiction of a human foot having hammertoe of the second toe in FIG. 1*a*, and of the same human foot after revision surgery using the apparatus of the preferred embodiment of the present invention in FIG. 1*b*.

Figure 2:
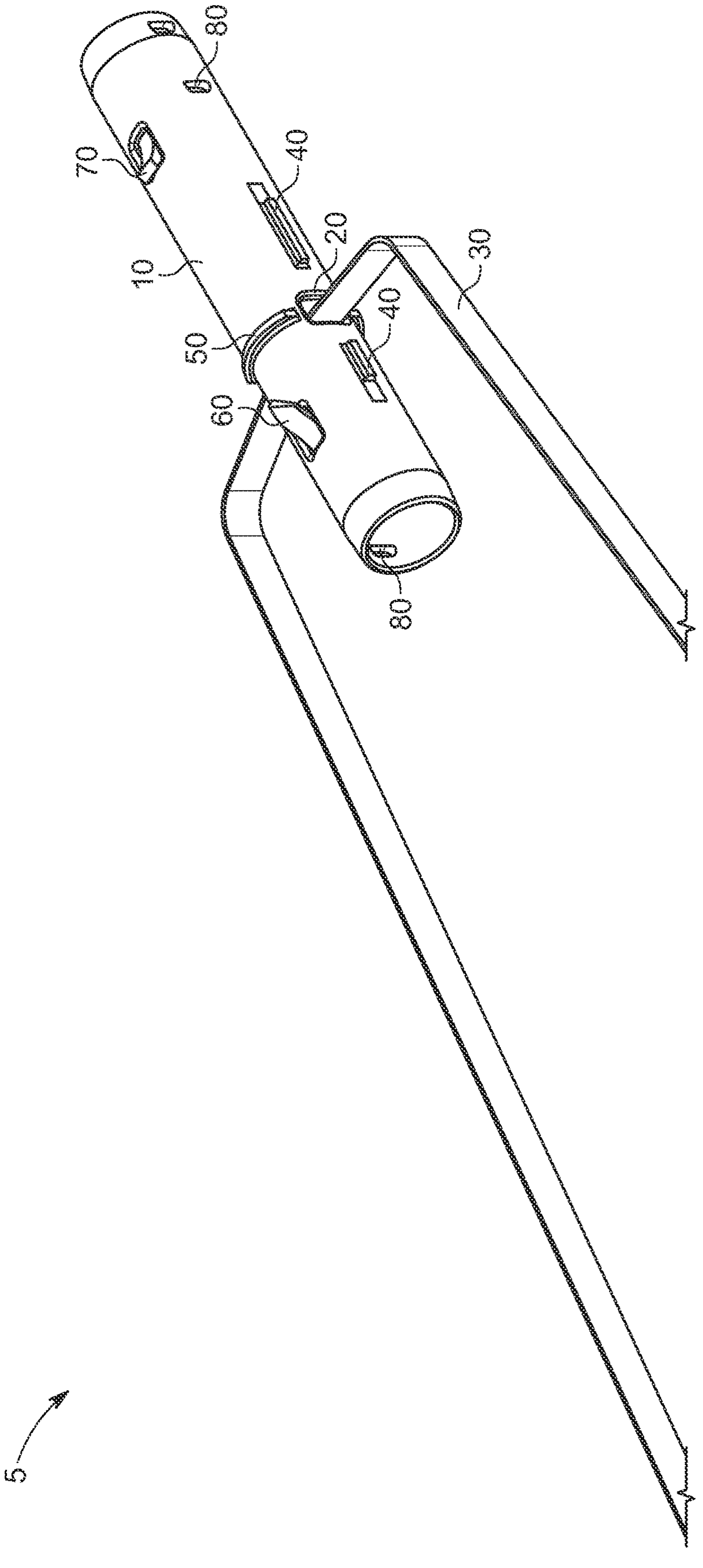
FIG. 2 is a 3D perspective view of an interphalangeal joint implant in accordance with a preferred embodiment of the invention.
Figure 4:
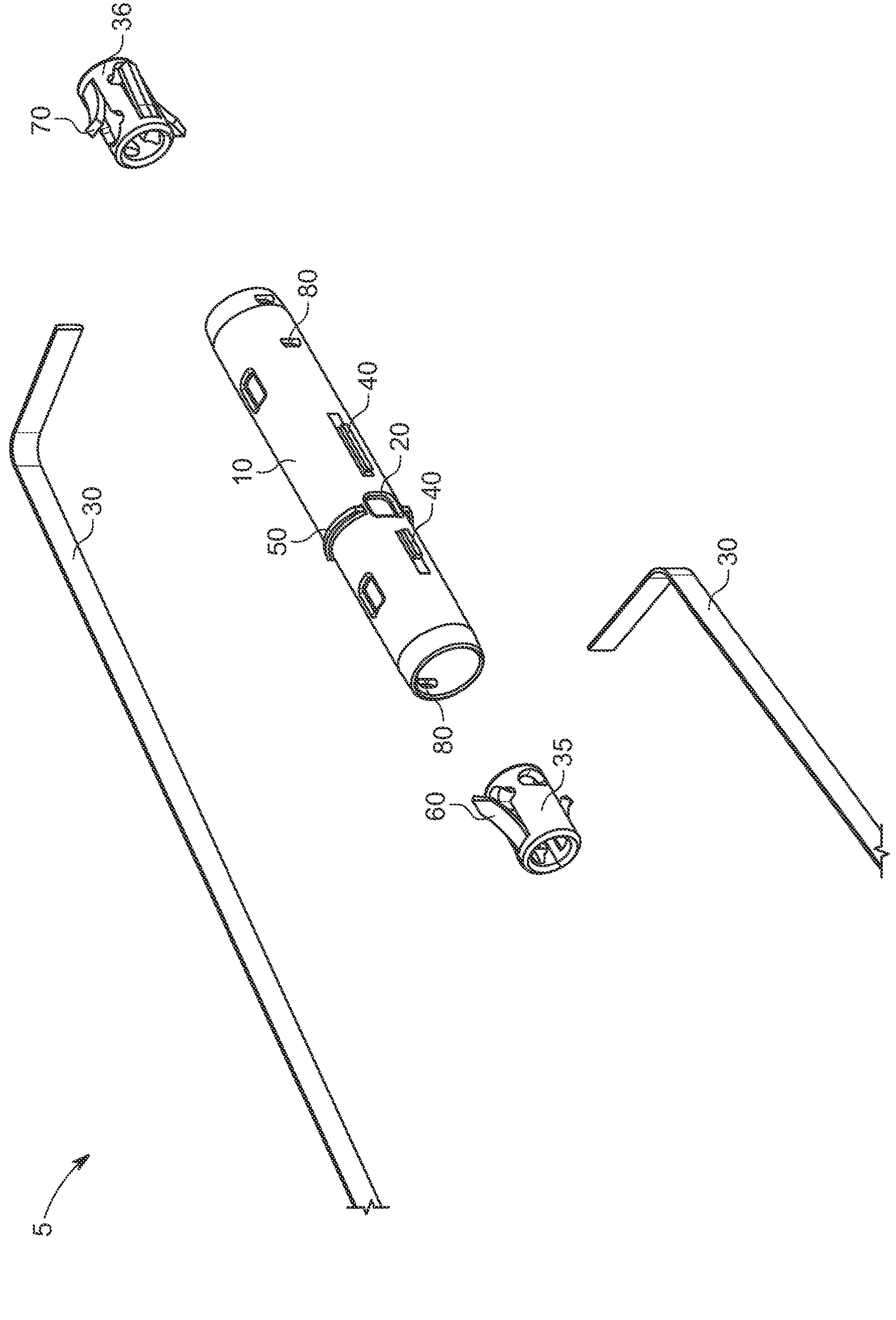
FIG. 4 is a perspective exploded schematic view of an interphalangeal joint implant in accordance with a preferred embodiment of the invention.

Referring now to FIGS. 2, 4, a preferred embodiment 5 comprises a cylindrical implant 10 having distal and proximal ends. Near each of the ends are provided two or more openings 20 from the lumen to the external surface of the cylinder. Within the lumen are disposed displaceable tines 60, 70, each aligned with an opening, and not protruding beyond the external surface. Each tine has a bone engagement end and a force receiving end, the force receiving end being disposed within the lumen. Also within the lumen are disposed two displacement elements 35, slidably contained within the lumen, and each having a tether 30 adapted to apply a sliding force to move the displacement element within the lumen to bring it into contact with the tines, thereby displacing the tines outward beyond the external surface. Optionally, each displacement element may also be provided with a further tether (or a continuation of the tether) adapted to displace the displacement element in the opposite direction, removing the force applied to the tines and allowing them to retract into their respective openings. A preferred embodiment places the tethers inside the lumen, and provides a port 20 located near the mid-point of the implant through which the tethers exit the lumen and may be pulled to exert force thereon. As shown, each of the tethers is a continuous ribbon having a molded handle or loop (not shown) which facilitates application of sufficient force to extend the associated tines to engage the lumen of the bone.

The external surface of implant 5 is provided with longitudinal ribs 40 to impede rotation of the implant after it is inserted into the bone. It is also provided with circumferential rib 50 to prevent the implant from being displaced further into the bone than intended.

Figure 3:
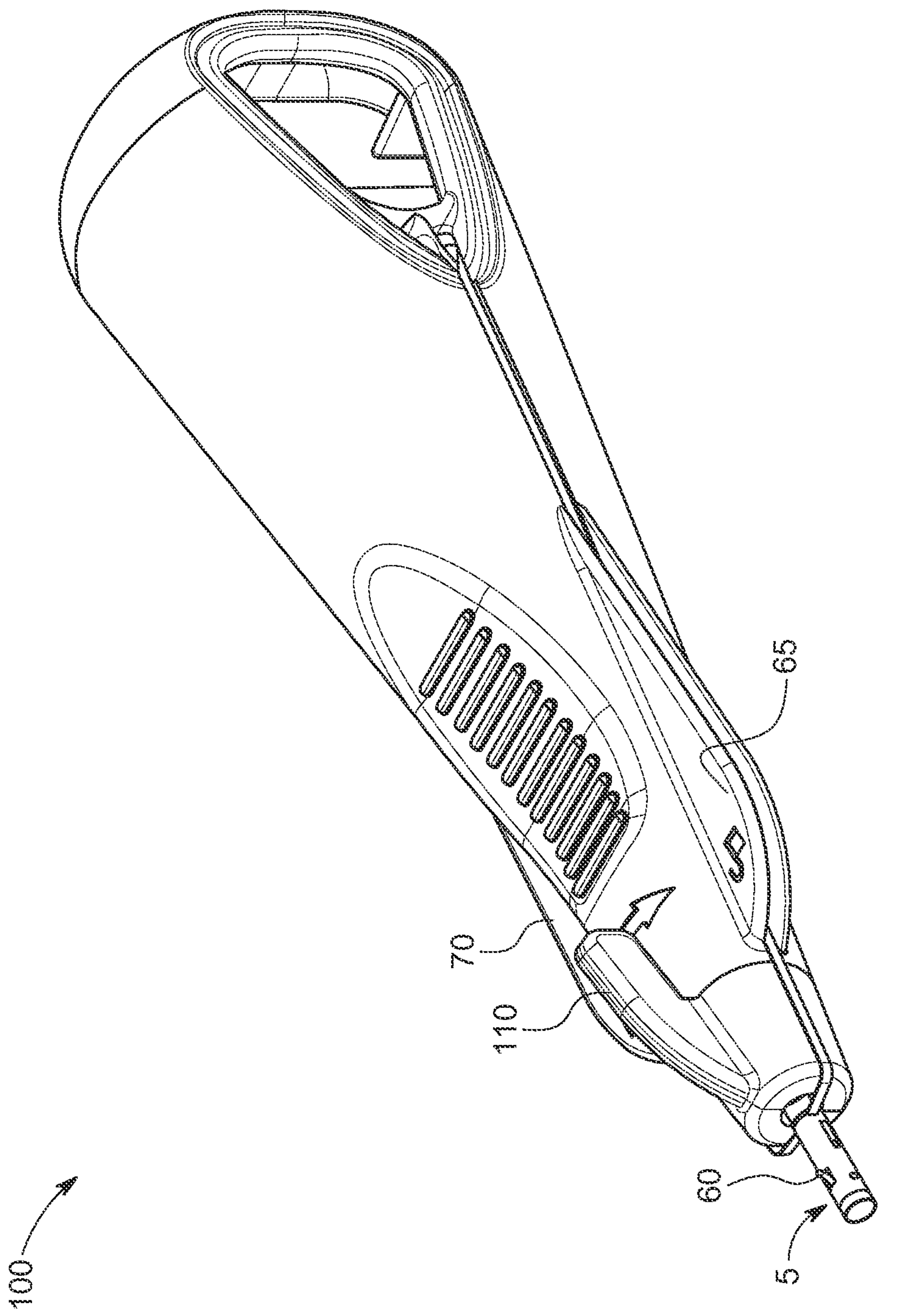
FIG. 3 is a 3D perspective view of an implant insertion tool in accordance with a preferred embodiment of the invention.

Referring now to FIG. 3, there is shown in perspective view an implant insertion tool 100 in accordance with a preferred embodiment of the invention. Tool 100 is a handle, into which implant 5 is lockably inserted, distal end first. Tethers 30 are arranged in channels 65, 70 and terminate in molded loops frictionally engaged in either side of the tool. Locking element 110 is rotatable in either a clockwise or anticlockwise direction after implant insertion to disengage the implant from the tool.

Figure 5:
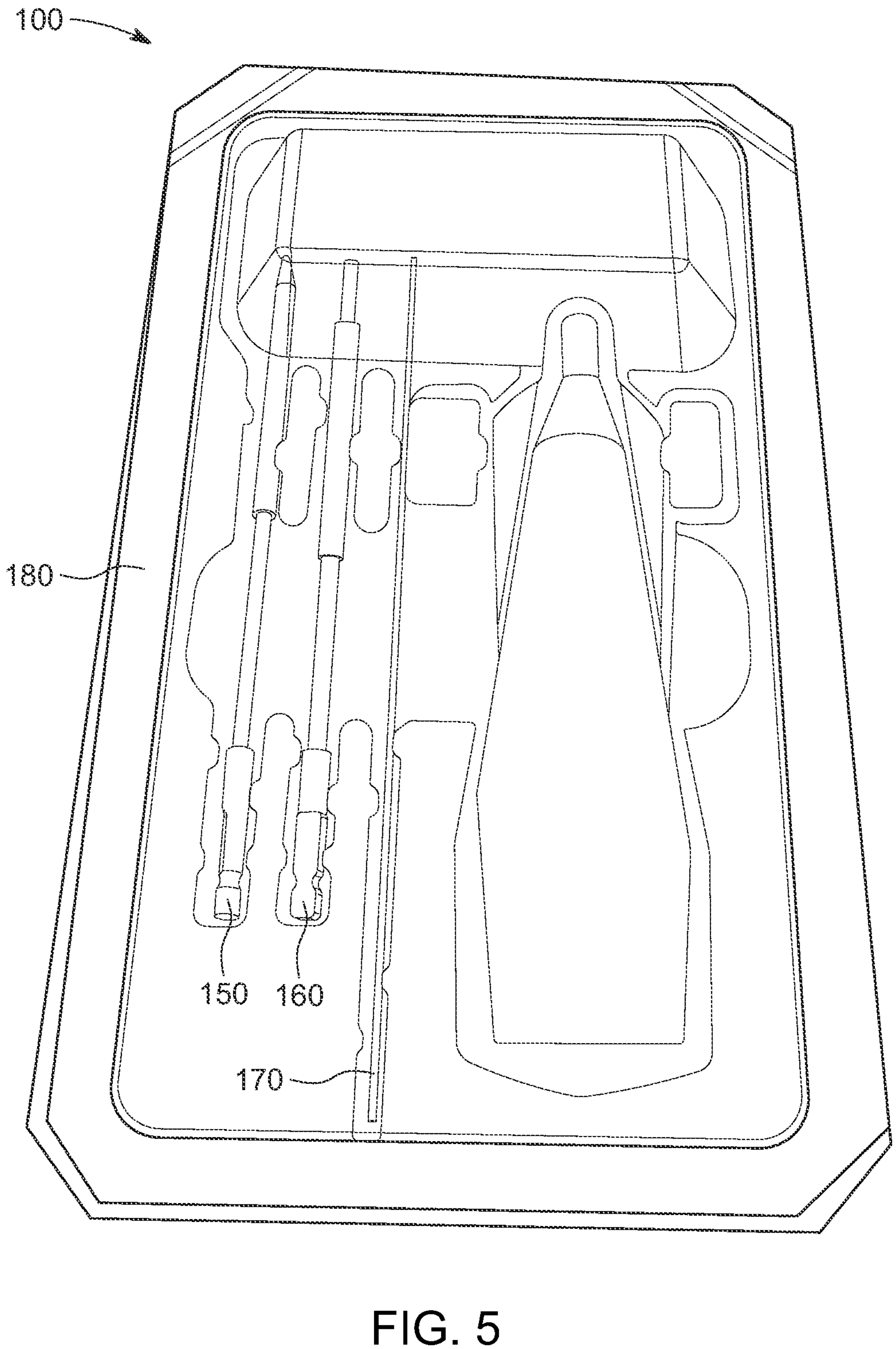
FIG. 5 is a schematic view of the surgical kit which incorporates of an interphalangeal joint implant loaded into an insertion tool, in accordance with a preferred embodiment of the invention as well as matched drills for preparation of the bones and optional K wire.

Referring now to FIG. 5 there is shown in schematic a surgical kit 100 comprising a plastic tray 110 covered by a lid 180, containing two drills 150, 160, and an implant according to the present invention preloaded into an inserter tool handle. Optionally a K wire 170 may be included in the kit. The several elements of the kit are sized according to the length and/or diameter of the bones to be treated, and it is anticipated that an inventory of various sizes will be stocked by the surgical facility to permit selection of the proper size for each patient's needs. Each of the drills is provided with a shoulder or stop dimensioned to prevent over-drilling the two bone ends, and each drill is typically color coded to reduce the probability of improper selection and use during surgery. Either as a part of the kit, or separately therefrom, a kit comprising a removal tool will be made available in the case that surgical revision is indicated. Each kit will be encased in a wrapper and delivered sterile using appropriate means of sterilization as practiced in the art of surgical kits.

The disclosure is directed to correction of misalignment between virtually any two bones, but particularly for the flange bones that make up the five digits of the foot and hands. A typical bone misalignment is characterized by dorsiflexion of the metatarsal/proximal phalangeal joint 108 and plantar flexion the proximal interphalangeal joint ("PIP"). The instant invention is directed to correction of this abnormal flexion of the PIP. Although the subject disclosure is directed in particular to medically correcting hammer toe syndrome it is also useful for more curved or claw toe maladies as well. In this sense the term hammer toe as used herein includes claw toe, mallet toe and curly toe conditions. The disclosure also applies to analogous conditions affecting human fingers.

Other structures can be added to the preferred embodiment to inhibit an unintended tendency for the device to loosen or slide out from the end of bone. For example, the surface of the cylinder may have various structures and shapes that promote tissue in -rowth such as interstitial spaces, ribs, channels, holes, grooves and the like.

In the preferred embodiment, the cylindrical element is provided with external fins or ribs intended to prevent rotation within the joint after implantation. Also in the preferred embodiment, the cylindrical element is provided with a partial circumferential rib or fin at the location of the joint to prevent displacement further into the bone after implantation.

The purpose of the preferred embodiment is to treat bones in an abnormal and sometimes dysfunctional position, such as a hammer toe, and to reestablish function. The bones must function properly throughout active motion of the foot as well as when the foot is at rest. To a first approximation, the functional position is to straighten the PIP joint, that is, the longitudinal axis of the proximal phalanx is in axial alignment with the longitudinal axis of the middle phalanx. This may not, in practice, be the optimal position for the PIP joint. In another preferred embodiment, a slight angle between these bones may be more functional for a patient. In this case the cylinder may be altered so that the PIP varies from straight to as much as 15° from linear.

While a preferred embodiment of the device is use in the PIP to correct hammer toe, the device is not limited solely to use with the lesser toes but can also be used in fingers as well as the thumb and great toe. Indeed, variations of the device can treat a wide variety of maladies related to improper bone alignment. A non-exhaustive list of examples includes: flexible and rigid hammer toe, deviated/crooked toes or fingers (caused by either physical injury or inherited) arthritic joints, claw toe, mallet toe and long toes requiring shortening (e.g. Morton's Toe). In addition, other embodiments of the invention comprise variations to address use as a suture anchor wherein the apparatus is press-fit into a predrilled hole completely, and the lateral tethers used for tine deployment are cut at the proximal ends, near the handles, and used to tie down various soft tissues. The apparatus of the present invention may also be employed in fracture management (e.g., Clavival Fracture) where an ORIF is being performed. The bone is drilled and prepared in a similar way to the osteotomy performed on PIPJ fusion, and the apparatus is used to reduce and hold continuous compression on that reduction. In the case of acromioclavicular and sacroiliac joint fusion The clavicle and acromion may be fused using the apparatus of the present invention.

A preferred material for the implant body is medical grade titanium. A preferred material for the implant tines is nitinol or a similar shape memory alloy. However, other medical grade materials may also be used.

Method of Treatment for Abnormal Flexion

The interphalangeal joint implant of the preferred embodiment is inserted using the following procedure. Using conventional steps as known and practiced in the prior art, a surgeon exposes the PIP, separates the two bones making up the joint and then removes the articular cartilage. The bones are then “cored”. According to the present invention, the provided drills are preferably used to core the ends of the bones on each side of the joint. The drill removes a central cylindrical section of bone within the bone shafts which allows for a press-fit of the implant.

The proximal end of the implant is inserted into the proximal phalanx and the distal end of the implant is inserted into the middle phalanx. The tethers are then tensioned, causing the displacement elements to extend the tines within the opposing bone shafts to lock each end of the implant in position, preventing both pull out and rotation. If stabilization of an adjacent joint is required, an optional k-wire can be directed from within the joint out through the tip of the toe.

According to a preferred embodiment of the present invention, the insertion of the implant and anchoring it in place are best performed with an insertion tool, as shown in FIG. 3. Tool handle 100 is provided with an aperture for receiving the joint implant of the present invention, with the distal end thereof engaged and locked in place within the aperture. Tethers 30 are disposed along opposing channels 65, 70 on the outer surface of handle 100, and are attached to pull rings which are frictionally retained within indentations on the outer surface of handle 100. Preferably, each pull ring is colored differently from the other pull ring to reduce the likelihood of confusion on the part of a surgeon.

In use, handle 100 is used to insert the implant into the proximal bone of the PIP, and tether pull ring is dislodged from its indentation and pulled to extend the tines locking the implant in place. Lock 110 is then disengaged to allow the implant to be released from handle 100. The distal phalanx is then positioned on the implant, and the other pull ring released and used to extend the tines locking the implant in place. By cutting the tethers and pulling each ring, the tethers may be fully withdrawn from the implant and the handle, tethers, and pull rings discarded.

After implantation, prior art methods of sterile wound closure may be employed to complete the procedure.

In the specification and claims herein, the expression “approximately” or “generally” are intended to mean at or near, and not exactly, such that the exact location or configuration is not considered critical unless specifically stated.

In describing the invention, reference has been made to preferred embodiments. Those skilled in the art however, and familiar with the disclosure of the subject invention, may recognize additions, deletions, substitutions, modifications and/or other changes which will fall within the scope of the invention as defined in the following claims.

While the invention has been described in its preferred embodiments, it is to be understood that the words which have been used are words of description rather than of limitation and that changes may be made within the purview of the appended claims without departing from the true scope and spirit of the invention in its broader aspects. Rather, various modifications may he made in the details within the scope and range of equivalents of the claims and without departing from the spirit of the invention. The inventors further require that the scope accorded their claims be in accordance with the broadest possible construction available under the law as it exists on the date of filing hereof (and of the application from which this application obtains priority, if any) and that no narrowing of the scope of the appended claims be allowed due to subsequent changes in the law, as such a narrowing would constitute an ex post facto adjudication, and a taking without due process or just compensation.

We claim as our invention:

1. An apparatus for treatment of a joint, the apparatus comprising:

a main body having a proximal end, a distal end, an outer wall extending from the proximal end to the distal end of the main body, and a lengthwise opening extending from the proximal end to the distal end of the main body;

at least two proximal openings passing through the outer wall near the proximal end of the main body;

at least two distal openings passing through the outer wall near the distal end of the main body;

a first displacement element slidably disposed within the lengthwise opening of the main body;

at least two proximal tines slidably disposed within the lengthwise opening of the main body and configured to be at least partially advanceable through the at least two proximal openings of the main body;

a first tether coupled with the first displacement element;

a second displacement element slidably disposed within the lengthwise opening of the main body;

at least two distal tines slidably disposed within the lengthwise opening of the main body and configured to be at least partially advanceable through the at least two distal openings of the main body;

a second tether coupled with the second displacement element;

wherein:

the at least two proximal openings are sized and configured to receive at least a distal portion of each of the at least two proximal tines therethrough; and the at least two distal openings are sized and configured to receive at least a distal portion of each of the at least two distal tines therethrough;

the main body comprises one or more ports through the outer wall of the main body;

the first tether extends from the first displacement element and out of the main body through the one or more ports in a pre-implanted state wherein the at least two proximal tines are positioned entirely within the lengthwise opening of the main body and the at least two distal tines are positioned entirely within the lengthwise opening of the main body; and the second tether extends from the second displacement element and out of the main body through the one or more ports in the pre-implanted state.

2. The apparatus of claim 1, further comprising one or more longitudinal ribs disposed on the outer wall of the main body.

3. The apparatus of claim 1, further comprising a circumferential rib disposed on the outer wall of the main body at a location for approximating a mid-point of a proximal interphalangeal joint.

4. The apparatus of claim 1, wherein the main body is comprised of a proximal segment and a distal segment, wherein an axis of the distal segment is displaced about ten degrees downward from an axis of the proximal segment when implanted.

5. The apparatus of claim 1, wherein the one or more ports comprises a first port and a second port positioned at or near a mid-point of the main body, wherein the first tether extends from the first displacement element and out of the main body through the first port and the second tether extends from the second displacement element and out of the main body through the second port.

6. The apparatus of claim 1, wherein:
the first tether comprises a first ribbon; and
the second tether comprises a second ribbon.

7. The apparatus of claim 1, wherein:
the at least two proximal tines point away from the proximal end of the main body such that a distal end of the at least two proximal tines is positioned further away from the proximal end of the main body than a proximal end of the at least two proximal tines; and
the at least two distal tines point away from the distal end of the main body such that a distal end of the at least two distal tines is positioned further away from the distal end of the main body than a proximal end of the at least two distal tines.

8. The apparatus of claim 1, wherein the first displacement element and the second displacement element each have a length less than a length of the main body.

9. The apparatus of claim 8, wherein the first displacement element and the second displacement element each have a length less than half of the length of the main body.

10. The apparatus of claim 1, wherein the apparatus is configured such that when the at least two proximal tines and the at least two distal tines are disposed entirely within the lengthwise opening of the main body:
the first displacement element is configured to move in a direction towards a mid-point of the main body when the first tether is pulled; and
the second displacement element is configured to move in a direction towards the mid-point of the main body when the second tether is pulled.

11. The apparatus of claim 1, wherein at least a portion of the main body is cylindrical.

12. The apparatus of claim 1, wherein the main body is generally cylindrical from the proximal end to the distal end of the main body.

13. The apparatus of claim 1, wherein the apparatus is adapted such that:
pulling the first tether causes the first displacement element to advance the at least two proximal tines at least partially through the at least two proximal openings; and
pulling the second tether causes the second displacement element to advance the at least two distal tines at least partially through the at least two distal openings.

14. A system including the apparatus of claim 1 and an insertion tool for surgical deployment of the apparatus of claim 1, comprising:
a handle having an outer surface;
an aperture at a distal end of the handle for receiving the distal end of the main body of claim 1;
a lock mechanism for retaining the main body in the aperture; and
two indentations on the outer surface of the handle adapted to frictionally retain pull rings attached to an end of each of the first tether and the second tether.

15. A method of treatment of a joint between a first bone and a second bone, the method, comprising:
preparing the joint for fusion;
inserting the proximal end of the main body of claim 1 into the first bone;
pulling the first tether to cause the first displacement element to advance the at least two proximal tines at least partially through the at least two proximal openings;
inserting the distal end of the main body into the second bone; and
pulling the second tether to cause the second displacement element to advance the at least two distal tines at least partially through the at least two distal openings.

16. The method of claim 15, wherein the joint is part of a human toe.

17. The method of claim 15, wherein the joint is part of a human finger.

18. The method of claim 15, wherein:
pulling the first tether comprises pulling the first tether through a first port of the one or more ports positioned at or near a mid-point of the main body to advance the at least two proximal tines at least partially through the at least two proximal openings; and pulling the second tether comprises pulling the second tether through a second port of the one or more ports positioned at or near a mid-point of the main body to advance the at least two distal tines at least partially through the at least two distal openings.

19. The method of claim 15, further comprising:
cutting the first tether and removing the first tether from the main body; and
cutting the second tether and removing the second tether from the main body.

20. The method of claim 15, wherein preparing the joint comprises exposing the joint, separating the first bone and the second bone, and coring an end of each of the first bone and the second bone with a drill to remove a central section from the end of each of the first bone and the second bone.

21. The method of claim 15, wherein:
pulling the first tether causes the at least two proximal tines to extend into the first bone; and
pulling the second tether causes the at least two distal tines to extend into the second bone.

22. The method of claim 21, wherein the first bone comprises a proximal phalanx and the second bone comprises a middle phalanx.

23. An apparatus for treatment of a joint, the apparatus comprising:
a main body having a proximal end, a distal end, an outer wall extending from the proximal end to the distal end of the main body, a lengthwise opening extending from the proximal end to the distal end of the main body, and one or more ports through the outer wall of the main body;
at least two proximal openings passing through the outer wall near the proximal end of the main body;
at least two distal openings passing through the outer wall near the distal end of the main body;
a first displacement element slidably disposed within the lengthwise opening of the main body;
at least two proximal tines slidably disposed within the lengthwise opening of the main body and configured to be at least partially advanced through the at least two proximal openings of the main body;
a first tether removably coupled with the first displacement element;

a second displacement element slidably disposed within the lengthwise opening of the main body;

at least two distal tines slidably disposed within the lengthwise opening of the main body and configured to be at least partially advanced through the at least two distal openings of the main body;

a second tether removably coupled with the second displacement element;

wherein:

the at least two proximal openings are sized and configured to receive at least a distal portion of each of the at least two proximal tines therethrough; and the at least two distal openings are sized and configured to receive at least a distal portion of each of the at least two distal tines therethrough.

24. The apparatus of claim 23, wherein the one or more ports comprises a first port and a second port positioned at or near a mid-point of the main body, wherein the first tether extends from the first displacement element and out of the main body through the first port and the second tether extends from the second displacement element and out of the main body through the second port.

25. The apparatus of claim 23, wherein the apparatus is configured such that, when the at least two proximal tines and the at least two distal tines are disposed entirely within the lengthwise opening of the main body:

the first displacement element is configured to move in a direction towards a mid-point of the main body when the first tether is pulled; and the second displacement element is configured to move in a direction towards the mid-point of the main body when the second tether is pulled.

26. The apparatus of claim 23, wherein:

the at least two proximal tines point away from the proximal end of the main body such that a distal end of the at least two proximal tines is positioned further away from the proximal end of the main body than a proximal end of the at least two proximal tines; and the at least two distal tines point away from the distal end of the main body such that a distal end of the at least two distal tines is positioned further away from the distal end of the main body than a proximal end of the at least two distal tines.

27. The apparatus of claim 23, further comprising a circumferential rib disposed on the outer wall of the main body at a location for approximating a mid-point of a proximal interphalangeal joint.

28. An apparatus for treatment of a joint, the apparatus comprising:

a main body having a proximal end, a distal end, an outer wall extending from the proximal end to the distal end of the main body, and a lengthwise opening extending from the proximal end to the distal end of the main body;

at least two proximal openings passing through the outer wall near the proximal end of the main body;

at least two distal openings passing through the outer wall near the distal end of the main body;

a first displacement element slidably disposed within the lengthwise opening of the main body;

at least two proximal tines slidably disposed within the lengthwise opening of the main body and configured to be at least partially advanced through the at least two proximal openings of the main body;

a first tether coupled with the first displacement element;

a second displacement element slidably disposed within the lengthwise opening of the main body;

at least two distal tines slidably disposed within the lengthwise opening of the main body and configured to be at least partially advanced through the at least two distal openings of the main body;

a second tether coupled with the second displacement element;

wherein:

the at least two proximal openings are sized and configured to receive at least a distal portion of each of the at least two proximal tines therethrough; and the at least two distal openings are sized and configured to receive at least a distal portion of each of the at least two distal tines therethrough;

the apparatus is configured such that pulling the first tether causes the first displacement element to advance the at least two proximal tines at least partially through the at least two proximal openings; and the apparatus is configured such that pulling the second tether causes the second displacement element to advance the at least two distal tines at least partially through the at least two distal openings.

29. The apparatus of claim 28, wherein the apparatus is configured such that, when the at least two proximal tines and the at least two distal tines are disposed entirely within the lengthwise opening of the main body:

the first displacement element is configured to move in a direction towards a mid-point of the main body when the first tether is pulled; and the second displacement element is configured to move in a direction towards the mid-point of the main body when the second tether is pulled.

30. The apparatus of claim 28, wherein the first displacement element and the second displacement element each have a length less than a length of the main body.

31. The apparatus of claim 28, wherein the at least two proximal tines point away from the proximal end of the main body such that a distal end of the at least two proximal tines is positioned further away from the proximal end of the main body than a proximal end of the at least two proximal tines; and the at least two distal tines point away from the distal end of the main body such that a distal end of the at least two distal tines is positioned further away from the distal end of the main body than a proximal end of the at least two distal tines.

32. The apparatus of claim 28, wherein the main body is comprised of a proximal segment and a distal segment, wherein an axis of the distal segment is displaced about ten degrees downward from an axis of the proximal segment when implanted.

* * * * *